(12) United States Patent
Swalwell

(10) Patent No.: US 10,107,746 B2
(45) Date of Patent: Oct. 23, 2018

(54) SYSTEM AND METHOD FOR IMMERSION FLOW CYTOMETRY

(71) Applicant: University of Washington, Seattle, WA (US)

(72) Inventor: Jarred E. Swalwell, Shoreline, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 15/540,011

(22) PCT Filed: Jan. 5, 2016

(86) PCT No.: PCT/US2016/012221
§ 371 (c)(1),
(2) Date: Jun. 26, 2017

(87) PCT Pub. No.: WO2016/112035
PCT Pub. Date: Jul. 14, 2016

(65) Prior Publication Data
US 2018/0011016 A1    Jan. 11, 2018

Related U.S. Application Data

(60) Provisional application No. 62/101,036, filed on Jan. 8, 2015.

(51) Int. Cl.
*G01N 21/49* (2006.01)
*G01N 15/14* (2006.01)
*G01N 15/10* (2006.01)

(52) U.S. Cl.
CPC ......... *G01N 21/49* (2013.01); *G01N 15/1434* (2013.01); *G01N 15/1459* (2013.01); *G01N 2015/1006* (2013.01)

(58) Field of Classification Search
CPC ............ G01N 15/147; G01N 15/1434; G01N 15/1463; G01N 2015/0065;
(Continued)

(56) References Cited

U.S. PATENT DOCUMENTS 2,037,014 A    4/1936  Eitzen
2,072,478 A    3/1937  Gray
(Continued)

OTHER PUBLICATIONS

International Preliminary Report on Patentability dated Jul. 20, 2017, issued in corresponding International Application No. PCT/US2016/012221, filed Jan. 5, 2016, 7 pages.
(Continued)

*Primary Examiner* — Michael P Stafira
(74) *Attorney, Agent, or Firm* — Christensen O'Connor Johnson Kindness PLLC; Ryan E. Dodge, Jr.

(57) ABSTRACT

An immersion cytometry system (200, 250) having a primary focusing optic immersed in a fluid stream (209) containing suspended particles (212). The system includes a light source (202) configured to illuminate a sensing region in the fluid stream that includes a focus of the primary optic. Light scattered and/or fluoresced from suspended particles passing through the sensing region is focused by an external tube lens on an external detector. The primary optic in one embodiment is a ball lens. In some embodiments, one or more filter/beam splitters on the optical axis reflect a portion of the signal light towards corresponding detectors, each filter being configured to reflect a preselected waveband of light.

4 Claims, 3 Drawing Sheets

(58) Field of Classification Search
CPC ....... G01N 2015/1006; G01N 15/1475; G01N 2015/1452; G01N 15/14; G01N 15/1404; G01N 21/6428; G01N 15/1456; G01N 21/645; G01N 33/5091
See application file for complete search history.

(56) References Cited

U.S. PATENT DOCUMENTS

| | | |
|---|---|---|
| 3,482,107 A | 12/1969 | Hock |
| 4,732,479 A | 3/1988 | Tanaka |
| 4,813,031 A | 3/1989 | Bierhoff |
| 5,133,602 A | 7/1992 | Batchelder |
| 5,350,695 A | 9/1994 | Colella |
| 5,353,073 A | 10/1994 | Kobayashi |
| 5,739,902 A | 4/1998 | Gjelsnes |
| 5,760,900 A | 6/1998 | Ito |
| 5,844,685 A | 12/1998 | Gontin |
| 6,697,163 B2 | 2/2004 | Fukuda |
| 6,982,785 B2 | 1/2006 | van den Engh |
| 7,110,192 B2 | 9/2006 | Sauter et al. |
| 7,315,357 B2 | 1/2008 | Ortyn |
| 7,410,809 B2 | 8/2008 | Goix |
| 7,728,974 B2 | 6/2010 | van den Engh |
| 8,223,445 B2 | 7/2012 | van den Engh |
| 8,467,054 B2 | 6/2013 | Swalwell |
| 2008/0018894 A1 | 1/2008 | Zu et al. |
| 2008/0186479 A1 | 8/2008 | Swalwell |
| 2011/0090500 A1 | 4/2011 | Hu et al. |
| 2011/0267604 A1 | 11/2011 | Swalwell |

OTHER PUBLICATIONS

International Search Report dated Apr. 22, 2016, issued in corresponding Application No. PCT/US2016/012221, filed Jan. 5, 2016, 2 pages.

SYSTEM AND METHOD FOR IMMERSION FLOW CYTOMETRY

CROSS-REFERENCE TO RELATED APPLICATION

This application claims the benefit of Provisional Application No. 62/101,036, filed Jan. 8, 2015, the entire disclosure of said application is hereby incorporated by reference herein.

BACKGROUND

The most abundant organisms in the world's oceans are photosynthetic microbes that are less than ~20 µm in size. The photosynthetic microbes—the phytoplankton—are believed to generate about 50% of the oxygen and organic matter produced on Earth each year and serve as the base of marine food webs.

Flow cytometry is a technology for counting and/or otherwise examining small particles, for example cells and the like, by passing a stream of fluid in which the particle are suspended through a detection apparatus. In modern flow cytometry systems the detection apparatus typically relies on detecting the optical response produced as the particles pass through an illumination region of the device. In some microbial flow cytometers, for example, individual particles pass through an illumination zone, or region of interest, at a rate on the order of one thousand cells per second. Detectors, gated electronically, measure the magnitude of a pulse representing the light scattered (and/or fluoresced) by the cells. The pulse magnitudes, or other properties, can then be processed to characterize the cells according to a particular parameter of interest. For example, the angular dependence of scattered light may provide information on the nature of the scattering particles. More importantly, in some applications the fluorescent properties of the detected particles, which may be caused by appropriate fluorophores added to the suspension, provide desired parametric information. Modern flow cytometers use coherent light to illuminate a region of interest in a carefully prepared fluid stream, and collect scattered and/or fluoresced light from particles in the stream to count and characterize the particles.

In recent years, flow cytometers have become an essential tool for oceanographic research. Flow cytometry led to the discovery of *Prochlorococcus*, believed to be the most abundant photosynthetic organism on Earth. Modern cytometry systems are able to rapidly and accurately characterize the abundance, size, and fluorescent characteristics of individual phytoplankton cells in a fluid stream.

The complexity of flow cytometry and the multi-parametric data it produces has hampered the application of flow cytometry to autonomous platforms. It would be advantageous to expand autonomous measurements of phytoplankton communities by developing a miniaturized low-power flow cytometer. Current underwater flow cytometer systems depend on a supply of clean water for instrument operation. In U.S. Pat. No. 8,773,661, to Swalwell, which is hereby incorporated by reference in its entirety, a virtual core technology is disclosed that enables direct cytometric measurements on a flow of raw seawater. This technology has been successfully implemented in a shipboard-based continuous flow cytometer.

The present inventor has developed a novel cytometer configured to autonomously and continuously measure the abundance and composition of microbial populations, for example phytoplankton cells (0.5-20 µm in size), in surface waters while underway aboard a ship. The cytometer is referred to as the SeaFlow cytometer. The system was designed for phytoplankton because these small cells dominate open ocean environments where the most abundant phytoplankton are *Prochlorococcus* (0.5 diameter), *Synechococcus* (2 µm diameter), other picoplankton (<2 µm in diameter), and nanoplankton (2-20 µm diameter). Shipboard, underway measurements were emphasized because it has been shown repeatedly that accurate descriptions of microbial community distribution and abundance require observations that occur at a higher frequency than the rate of cell division or mortality, or the rate of environmental changes. A defining feature of SeaFlow is an optical system development known as virtual core flow cytometry. Virtual core flow cytometry detects particles suspended throughout a relatively larger stream, and discriminates between signals obtained from particles that are in a relatively narrow region of interest, i.e., in a focus region for the optical system, and particles that are not in focus. Virtual core flow cytometry eliminates the need to produce a very small diameter stream with suspended particles that is surrounded by a clear sheath fluid. In the SeaFlow cytometer, measurements are performed within a 200 µm diameter stream of 100 µm filtered seawater, which enables the taking of continuous cytometric measurements.

For more widespread use of virtual core cytometry systems, and in particular to the integration of such systems in autonomous platforms, improvements in reliability, lower costs, smaller size, and reduced power consumption are desirable.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

A flow cytometry system is disclosed that includes a light source, for example a laser, that is configured to direct light into or through a sensing region in a fluid stream containing suspended particles of interest. A primary focusing optic, for example a ball lens, is at least partially submerged in the fluid stream, and positioned to receive and focus light scattered by particles suspended in the stream as they pass through the sensing region. A tube lens is positioned to receive light from the primary optic, and focuses the light onto a photo detector, defining an optical axis aligned with the photo detector. The photodetector is configured to generate a signal responsive to the light and to transmit the signal to a signal processing system.

In an embodiment the primary focusing optic is a ball lens, for example, a glass ball lens. In an embodiment the primary focusing optic is a flint glass ball lens.

In an embodiment the primary focusing apparatus is configured to chromatically distort the light, such that the focus location varies with the light wavelengths.

In an embodiment the light source comprises a laser.

In an embodiment during operation the primary optic is immersed in a fluid stream having a diameter of at least 4 mm.

In an embodiment the system further includes a position-sensitive detector configured to identify a responsive signal corresponding to a particle in a particular region of interest within the sensing region, to identify responsive signals corresponding to particles that are not within a focal region of the primary focusing optic.

In a particular embodiment the system further includes a beam splitter, for example a filter/beam splitter, on the optical axis between the primary optic and the photodetector, wherein a portion of the light from the tube lens is directed to a second photo detector. For example a plurality of filter/beam splitters may be included to deflect light within preselected wavelength bands to corresponding photo detectors.

In an embodiment the primary optic, the tube lens, and the photo detector are fixedly connected in a desired alignment, and are pivotably mounted to a channel containing the fluid stream.

A flow cytometry system for analyzing a fluid stream having particles suspended therein includes a light source directed into a sensing region in the fluid stream, and a primary optic at least partially immersed in the fluid stream, and positioned to receive light scattered by particles passing through the sensing region. A tube lens is positioned to form an optical axis with the primary optic, and receives light from the primary optic. A position-sensitive detector having a first field stop, a light deflector, and a photo detector is configured to identify signals for particles that are not in a particular region of interest within the sensing region. A first chromatic filter/beam splitter is positioned along the optical axis and configured to direct a portion of light transmitted along the optical axis to the first field stop, and a first photo detector is configured to receive light directed to the first field stop that is not deflected by the light deflector. A second chromatic filter/beam splitter positioned along the optical axis configured to direct a portion of light from the optical axis to a second field stop, and a second photo detector configured to receive light focused on the second field stop, wherein the first chromatic filter/beam splitter has a different center wavelength than the second chromatic filter/beam splitter. The first photo detector and the second photo detector are configured to generate a signal responsive to the received light and to transmit the generated signals to a processing system.

In an embodiment the primary focusing optic comprises a ball lens, which may optionally be formed from a glass or sapphire.

A method for performing flow cytometry in a fluid stream having a plurality of particles suspended therein, includes providing a cytometer, as described above, and directing light from the light source of the cytometry system along the fluid stream to a sensing region in the fluid stream where the primary focusing optic of the cytometry system is at least partially immersed in the fluid stream and positioned to receive light from the light source passing through the sensing region.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
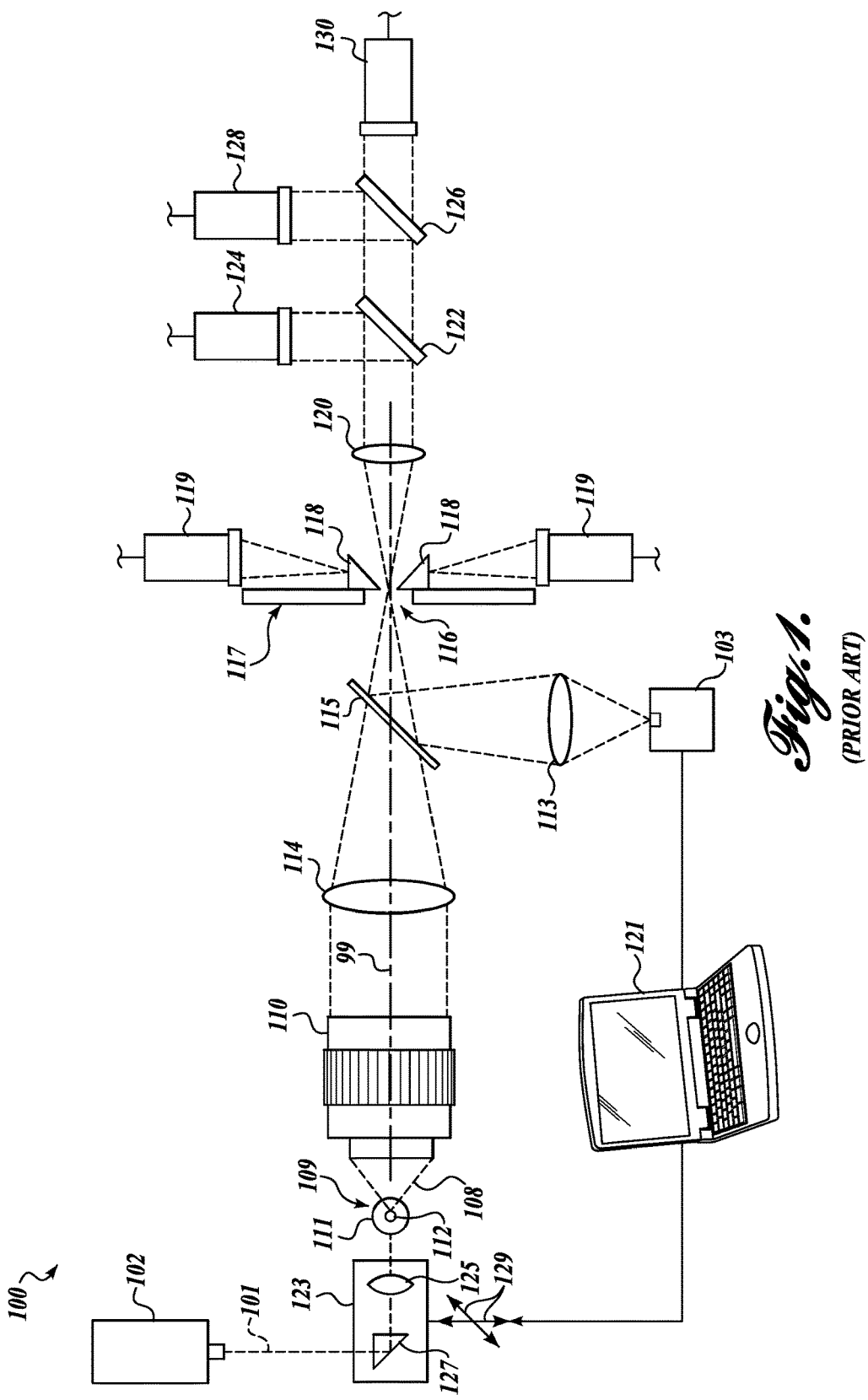
FIG. 1 shows a prior art flow cytometry system that includes continuous automated alignment.

An exemplary prior art position-sensitive virtual core flow cytometry system 100 incorporating an auto-alignment component is shown in FIG. 1, and is taken from U.S. Pat. No. 8,928,881, to Swalwell, which is hereby incorporated by reference. A fluid stream 109 containing particles 112 of interest (for example, cells) flows through a sensing region 111 (in FIG. 1 the direction of flow is perpendicular to the figure). One or more light sources 102, typically but not necessarily lasers, project light 101 through the sensing region 111. The projected light 101 interacts with the particles 112 as they pass through the sensing region 111, e.g., scattering the light 101 and/or inducing particles to fluoresce. A portion of the light 108 exiting the sensing region 111 is received by a primary focusing optic comprising an objective 110 and focused by a lens 114 through an optical aperture 116 in a field stop 117. The objective 110 and the lens 114 define the optical axis 99 for the system 100.

This system 100 includes a position-sensitive detector, for discriminating between signals from particles that are in the region of interest (the focus region for the objective 110) and particles that are not in the region of interest. Light deflectors 118 extending from the edges of the aperture 116 are configured to direct at least a portion of light incident on the light deflector 118 towards associated peripheral light photo detectors 119, for example, photomultiplier tubes (PMTs). Light that passes through the optical aperture 116 and is not deflected by the deflectors 118 passes through a lens 120 and is directed towards a first light detector 130. The system 100 may further include one or more beam splitters and/or filters 122, 126 that direct a portion of the light from the lens 120 toward additional light detectors 124, 128. For example, some of the particles in the fluid stream 109 may be induced by the light source 102 to fluoresce at a particular wavelength. One or more of the filters and/or light detectors may be configured to detect the fluorescent wavelength.

The peripheral photo detectors 119 provide a means for identifying light signals having a significant component incident on the light deflectors 118. This information may be used to selectively identify and/or exclude data received by the light detectors 124, 128, 130. For example, in an exemplary system, the light resulting from interactions of particles 112 in the sensing region 111 that are not in a focal area of the sensing region 111 produces a larger light component incident on the light deflectors 118 and therefore produces a larger signal from the peripheral photo detectors 119. The larger signals from the peripheral detectors can therefore be used to identify corresponding signals in the light detectors 124, 128, and 130 that are not in the focal region, and such signals may be excluded from further analysis.

In the system 100, a beam splitter 115 is positioned on the optical axis 99, and disposed between the lens 114 and the field stop 117. The beam splitter 115 allows most of the light from the lens 114 to pass through towards the aperture 116 and reflects a small portion of the light through a lens 113 towards a suitably positioned imaging device 103, for example, a CCD video camera, to produce an image of the field stop 117. To improve the image the field stop 117 preferably has a mirrored surface facing the beam splitter 115. Although a simple substantially transparent beam splitter 115 is used in a current embodiment, as used herein, "beam splitter" is defined to include other suitable optical elements, including, for example, a dichroic mirror/filter for which only a small band or range of frequency (some portion of that small band) is deflected towards the camera, this band being used for beam position information and allowing other bands to pass through substantially unaffected. The dichroic filter is advantageous because it is desirable to allow as much of the light information as possible to pass through the field stop aperture.

The imaging device 103 is in signal communication with a computing apparatus 121 and transmits the image data of the field stop 117 (through reflection from the beam splitter 113) to the computing apparatus 121. The image data is processed by the computing apparatus 121, and control signals are sent from the computing apparatus 121 to an XY stage 123 comprising servomotors (indicated by arrows 129) that adjust the position of the XY stage 123. In the system 100, the beam from the light source 102 is directed towards the sensing region 111 through a light deflector 127 (for example, a prism) and a lens 125 that are mounted on the XY stage 123. The signals from the computing apparatus 121 command the servomotors 129 to position the XY stage 123 for up-down motion and side-to-side motion.

Figure 2:
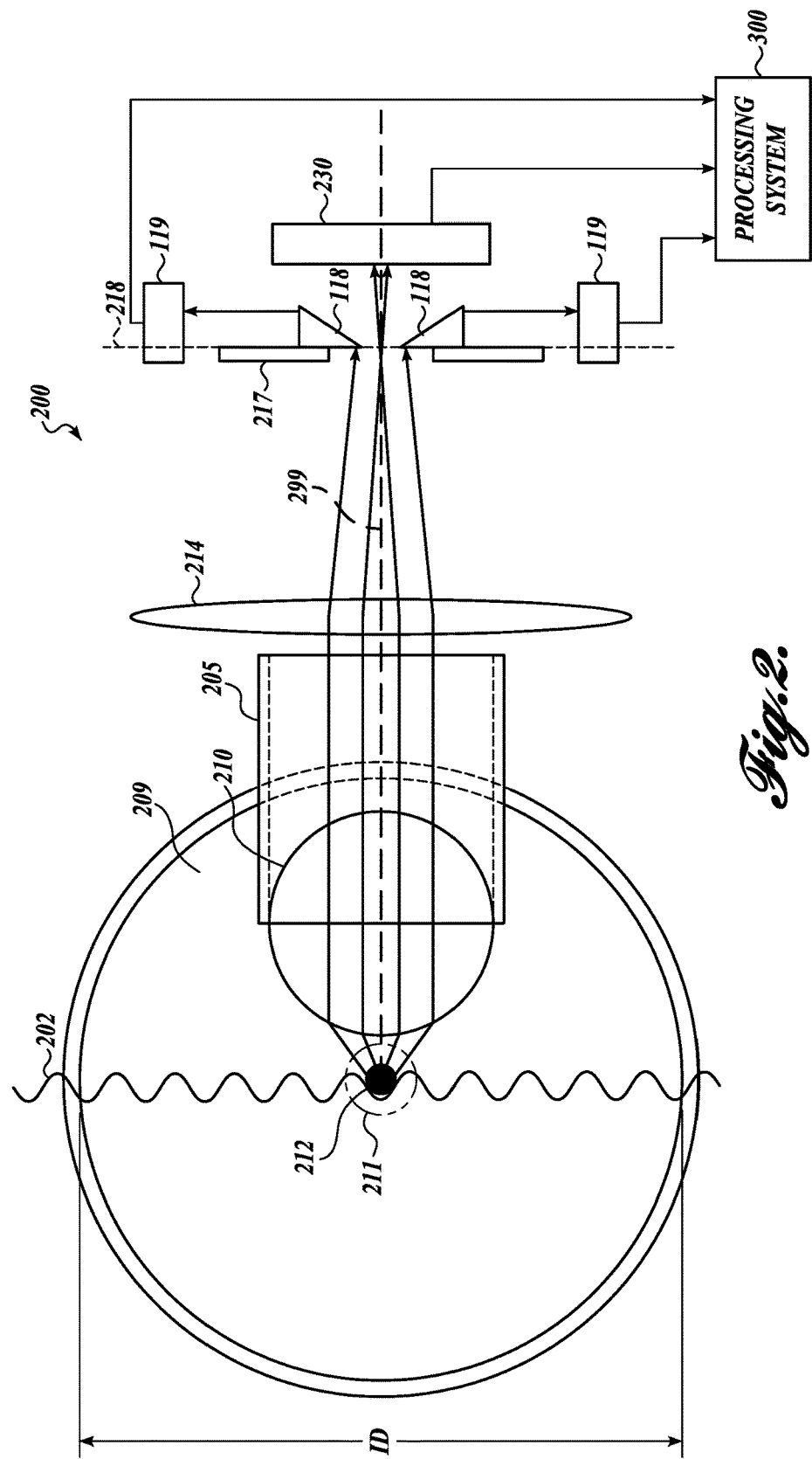
FIG. 2 shows a first embodiment of a flow cytometry system in accordance with the present invention.
Figure 3:
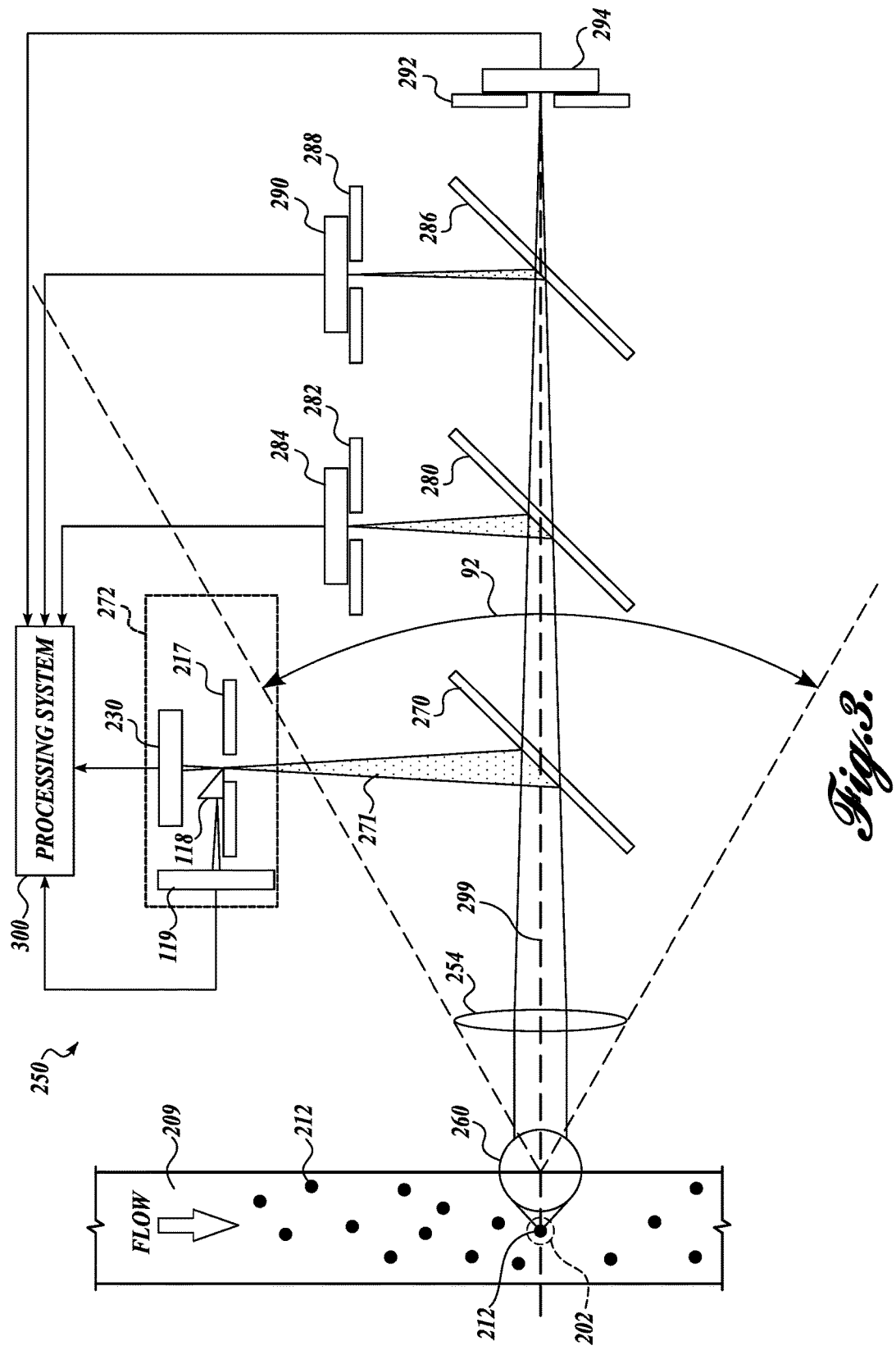
FIG. 3 shows a second embodiment of a flow cytometry system in accordance with the present invention.

A flow cytometer 200 in accordance with the present invention is shown in one embodiment in FIG. 2, and in another embodiment in FIG. 3.

A novel aspect of the flow cytometer 200 shown in FIG. 2 is that the primary focusing optic is not a conventional external objective lens system. Instead, a primary focusing optic 210 is immersed directly in a flow stream 209 to be analyzed (illustrated in cross-section transverse to the flow direction), thereby eliminating sub-millimeter scale fluid paths. In applications directed to oceanographic flow cytometry, for example, the flow stream 209 may comprise seawater. Immersing the primary focusing optic 210 in the flow stream 209 provides many advantages, as discussed in more detail below.

In this embodiment the primary focusing optic comprises a ball lens 210 that is supported in a lens housing 205. As will be obvious to persons of skill in the art, it is counter-intuitive to use a ball lens in imaging applications because of the severe geometrical and chromatic distortion associated with such lenses. However, in the flow cytometer 200 scattered and fluoresced light is collected primarily from a small region in the field, in this case along the optical axis 299 defined by the ball lens 210 and an associated tube lens 214. Geometrical distortion is at a minimum along this axis 299, and defocusing from minimal geometric distortion does not hamper photon collection. In an optional embodiment, the ball lens 210 is formed from a high index of refraction glass. The chromatic distortion from the high index of refraction glass causes collected light to be focused by the tube lens 254 onto different planes along the optical axis 299, based on the wavelength of the light.

The ball lens 210 extends into, and is at least partially immersed in, the flow stream 209. A coherent light beam 202 is transmitted through the flow stream 209 and illuminates a region of interest 211 near to the ball lens 210. The ball lens 210 receives scattered light and possibly fluorescence light from particles 212 interacting with the coherent beam 202 as they pass through the region of interest 211. The tube lens 214 located outside of the flow stream 209 is positioned to receive and focus parallel light received onto an image plane 218 on the optical axis 299. A field stop 217 is located at the imaging plane 218. Optionally, light deflectors 118 and peripheral photo detectors 119 provide position sensitivity, to identify light signals received from particles that were not in the region of interest 211 (e.g., not in focus). A distal photo detector 230 receives the light signals, for further conventional cytometric analysis.

The peripheral photo detectors 119 and the photo detector 230 generate signals responsive to the detected light signals. The generated signals are transmitted to a conventional processing system 300, for example a general purpose or special purpose computer, and identification (counting) and/or characteristics of the detected particles may be determined using conventional cytometry methods.

The flow cytometer 200 uses a large diameter (ID) fluid stream 209, greatly reducing or eliminating clogging issues that are a major challenge in conventional cytometry systems. In exemplary embodiments the cytometer flow stream has a diameter between 4 mm and 10 mm, and in a particular embodiment the flow stream has a diameter of about 7 mm.

The immersed primary focusing optic 210 is simpler to maintain and is much less expensive than a conventional objective. The larger diameter flow stream 209 can use the same anti-fouling strategies as other bulk measurements currently performed on other autonomous platforms. Immersing the primary focusing optic 210 also increases measurement sensitivity, which in turn reduces the power requirement for the excitation source. Unlike a standard flow cytometer optical system where the analyte is contained in a sheath fluid and placed well away from high-power and long focal length optics, the immersed optic system disclosed herein leverages the large light collection angle of a short focal length using a single inexpensive and expendable ball lens 210.

Another flow cytometer 250 in accordance with the present invention is shown in FIG. 3. The primary focusing optic is a ball lens 260 having a high index of refraction, for example a ball lens formed from flint glass. The ball lens 260 is partially immersed in the flow stream 209, which may comprise one or more liquids or gasses. In oceanographic applications the flow stream may be seawater.

As particles 212 pass through the region of interest and are illuminated by the coherent beam 202, the primary focusing optic 260 (immersed in the flow stream 209) receives scattered and/or fluorescent light from the illuminated particle 212. A tube lens 254 is positioned to receive light from the primary focusing optic 260 and to focus the received light along an optical axis 299 onto a detector 294.

Although a ball lens is currently preferred for the primary focusing optic 260, other short focal length lens shapes and configurations may be used for the immersed primary focusing optic 260, and are contemplated in accordance with the present invention, including, for example, a short focal length spherical lens. In a current embodiment the primary focusing optic 260 is a single ball lens 260, and in a more particular embodiment the ball lens formed from a high index of refraction glass.

In a conventional cytometer using a fixed pinhole position through which all light is gathered, such chromatic distortion may have a severe undesirable effect on performance. In the immersed lens systems disclosed herein, wherein the received light is not constrained by a pinhole aperture, the chromatic distortion may be leveraged to separate wavebands. The wavebands corresponding to the incident scattered light and the fluorescent detection are first separated by optical filters/beam splitters that direct the desired wavebands to separate, independent field stops.

For example, in FIG. 3 a first chromatic filter/beam splitter 270 is positioned on the optical axis 299 and configured to reflect a portion of the light 271 to a position-sensitive detector 272 including the first photo detector 230. As will be understood from FIG. 1 and the related discussion above, the position-sensitive detector 272 includes a field stop 217 with one or more light deflectors 118 configured to deflect off-centered light toward corresponding peripheral light photo detectors 119 to identify light signals from particles that are not within the desired region of interest. The first chromatic filter/beam splitter 270 is selected to filter and reflect the scatter light. The photo detector 230 receives the centered light for further cytometric analysis. A second chromatic filter/beam splitter 280 reflects a portion of the light, for example to detect a blue waveband, through field stop 282 and onto a second photo detector 284. A third chromatic filter/beam splitter 286 reflects a portion of the light, for example to detect a green waveband which may be useful for certain fluorescent detection, through another field stop 288 and onto a third photo detector 290. Remaining light is directed through another field stop 292 and focused onto a fourth photo detector 294, for example to detect a red waveband.

The collected light is therefore separated into wavebands, each of which has its own field stop placed at a desired position. The field stops are designed to allow positioning along the horizontal and vertical axis for alignment to each other, as well as for alignment with respect to the object plane. Therefore, the optical system can be aligned to collect light from anywhere in the object plane (in the flow stream 209) simply by aligning the field stops to that region in the image plane, as indicated by arrows 92.

The wavebands corresponding to the incident scattered light and fluorescent detection are first separated by the optical filters 270, 280, 286 that direct light towards associated field stops 217, 282, 288 and correspond to the center wavelength of the desired waveband. The advantage is that noise normally produced by scattered light is not in focus at the fluorescent field stops, and its resulting contribution to noise in the system is therefore significantly lower.

It will be appreciated that in systems in accordance with the present invention, because the primary focusing optic 210, 260 is immersed in the flow stream 209, a much higher numerical aperture (NA) of the optical system can be achieved than what is available with conventional flow cytometers. The improved NA is primarily due to the shorter focal length of the primary focusing optic, and more advantageous matching of refractive indexes between the scattering medium (the flow stream 209) and the collection optics (the immersed lens, for example the ball lens 210, 260).

In conventional flow cytometers, light that unavoidably scatters off of a measurement stream, cuvette, or flow cell contributes significantly to the background noise of the instrument. Although this noise may be partially controlled with light-obstructing components in the optical system, in the immersed flow cytometer systems 200, 250 described above, the primary optic 210, 260 and particles of interest are both immersed in the same fluid with no intervening boundaries that would introduce errant scatter and the resulting background noise. The reduction in background noise will result in improved sensitivity of the system 200, 250.

It is contemplated that the system 200, 250 may be modified to be immersed directly in a larger flow of fluid, measuring a sample directly without taking a circuitous path through the internals of an instrument. Such measurement may be considered "non-contact" measurements, which avoids issues related to contamination or other sampling errors resulting from transport of the fluid to a secondary measurement chamber.

It is contemplated that the primary optic 210, 260 may be designed to operate in very harsh environments. For example, the primary optic may be constructed from a suitably transparent material such as sapphire, which has very high mechanical strength and is resistant to chemicals and other hazards such as heat and abrasion.

Although applications related to oceanographic studies are discussed above, it will be appreciated that the disclosed immersion flow cytometer may be applied in different fields, for example, environmental monitoring, waste-water or drinking-water monitoring, industrial process monitoring including harsh chemical or physical environments, space exploration, or the like. In at least some of these applications, the disclosed immersion flow cytometer may be used with gasses, for example for monitoring air quality or the like.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

The following definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition, or a dictionary known to those of skill in the art, such as the Oxford Dictionary of Biochemistry and Molecular Biology (Ed. Anthony Smith, Oxford University Press, Oxford, 2004).

As used herein and unless otherwise indicated, the terms "a" and "an" are taken to mean "one", "at least one" or "one or more". Unless otherwise required by context, singular terms used herein shall include pluralities, and plural terms shall include the singular.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to." Words using the singular or plural number also include the plural and singular number, respectively. Additionally, the words "herein", "above", and "below", and words of similar import, when used in this application shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

All of the references cited herein are incorporated by reference. Aspects of the disclosure can be modified, if necessary, to employ the systems, functions, and concepts of the above references and application to provide yet further embodiments of the disclosure. These and other changes can be made to the disclosure in light of the detailed description.

Specific elements of any foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The embodiments of the invention in which an exclusive property or privilege is claimed are defined as follows:

1. A flow cytometry system for analyzing a fluid stream having particles suspended therein, the system comprising:
   a light source directed into a sensing region in the fluid stream;
   a primary focusing optic at least partially immersed in the fluid stream and positioned to receive light scattered by particles passing through the sensing region;
   a tube lens positioned to focus light received from the primary focusing optic, wherein the tube lens and the primary focusing optic define an optical axis;
   a position-sensitive detector configured to identify light focused by the tube lens corresponding to particles suspended in the fluid stream that are not in a region of interest within the sensing region, the position-sensitive detector comprising a first field stop with a light deflector, and a peripheral light photo detector configured to receive light deflected by the light deflector;
   a first chromatic filter/beam splitter positioned along the optical axis, the first chromatic filter/beam splitter configured to direct a portion of light transmitted along the optical axis to the first field stop;
   a first photo detector configured to receive light directed to the first field stop that is not deflected by the peripheral light photo detector;
   a second chromatic filter/beam splitter positioned along the optical axis configured to direct a portion of light from the optical axis to a second field stop;
   a second photo detector configured to receive light focused on the second field stop, wherein the first chromatic filter/beam splitter has a different center wavelength than the second chromatic filter/beam splitter;
   wherein the first photo detector and the second photo detector are each configured to generate a signal responsive to the received light and to transmit the generated signals to a processing system.

2. The cytometry system of claim 1, wherein the primary focusing optic comprises a ball lens.

3. The cytometry system of claim 1, wherein the primary focusing optic is formed from at least one of glass or sapphire.

4. A method for performing flow cytometry of a fluid stream having a plurality of particles suspended therein with a cytometer, the method comprising:
   providing the cytometry system of claim 1; and
   directing light from the light source of the cytometry system along the fluid stream to a sensing region in the fluid stream where the primary focusing optic of the cytometry system is at least partially immersed in the fluid stream and positioned to receive light from the light source passing through the sensing region.

* * * * *